United States Patent [19]

Morioka et al.

[11] Patent Number: 4,650,457

[45] Date of Patent: Mar. 17, 1987

[54] APPARATUS FOR EXTRACORPOREAL LUNG ASSIST

[75] Inventors: Tohru Morioka; Hidenori Terasaki, both of Kumamoto; Hiroyuki Akasu, Kurashiki; Akiyoshi Nakano, Okayama; Kohichi Takase, Ichikawa, all of Japan

[73] Assignee: Kuraray Co., Ltd., Kurashiki, Japan

[21] Appl. No.: 766,751

[22] Filed: Aug. 16, 1985

[51] Int. Cl.⁴ ............................................. A61M 1/03
[52] U.S. Cl. ................................ 604/4; 128/DIG. 3; 422/45
[58] Field of Search ....................................... 604/4–6, 604/245–246, 153; 128/1 D, DIG. 3; 422/45

[56] References Cited

U.S. PATENT DOCUMENTS

| | | | |
|---|---|---|---|
| 2,845,929 | 8/1958 | Strumia | 604/246 X |
| 3,883,272 | 5/1975 | Puckett et al. | 128/DIG. 3 |
| 4,466,804 | 8/1984 | Hino | 604/4 |
| 4,474,538 | 10/1984 | Schmid-Schobein | 604/4 X |
| 4,552,552 | 11/1985 | Polaschegg et al. | 128/1 D X |

*Primary Examiner*—Dalton L. Truluck
*Attorney, Agent, or Firm*—Kramer and Brufsky

[57] ABSTRACT

An apparatus for extracorporeal lung assist including a pump device having a flexible blood reservoir housed in a rigid housing, which pump device is able to expand and contract the blood reservoir by pumping liquid into and from the housing, thereby repeating cycles of blood feed and blood take-off, a blood take-off circuit connected to the in-flow side of a membrane artificial lung and in which the pump device is disposed, a blood feed circuit connected to the out-flow side of the membrane artificial lung, the two circuits forming an extracorporeal circulation circuit, a liquid circulation circuit connected to the housing of the pump device and having a flexible liquid reservoir disposed therein with a head provided relative to the pump device, and sensors for detecting the expansion and contraction of the liquid reservoirs, whereby blood in-flow and out-flow paths are controlled so that when the blood reservoir is contracted, blood is drawn into the blood reservoir under subpressure in the housing, whereas when the blood reservoir is expanded, blood is discharged from the blood reservoir under pressure developed in the housing. The apparatus of the invention provides respiratory aids safely for a long period of time and is therefore useful for treatment of acute respiratory failure cases.

10 Claims, 8 Drawing Figures

APPARATUS FOR EXTRACORPOREAL LUNG ASSIST

BACKGROUND OF THE INVENTION

1. Field of the Invention

The present invention relates to an apparatus for extracorporeal lung assist (ECLA) utilizing a membrane artificial lung and which is able to automatically control blood suction and feed by expanding and contracting a blood reservoir through liquid pressure. Unlike a pump oxygenerator which artificially performs lung functions for a short period of time, the apparatus in accordance with the invention provides respiratory aids safely for long (i.e., over a period of several days or even several weeks) and therefore it is useful for treatment of acute respiratory failure cases.

2. Description of Prior Art

Membrane artificial lungs employed in treating acute respiratory failure cases may be classified into three types, namely, coil type, plate type, and hollow fiber type, according to their structural characteristics. Such artificial lung is usually employed either in a double pump system or in a single pump system. The single pump system is advantageous over the double pump system in that the entire circuit involved is smaller in length, and in that less priming volume is involved, and further in that the system is easier to operate and less liable to danger due to malfunction. Yet, the single pump system leavs much to be desired. That is, a single-pump system apparatus which involves a further reduced priming volume is strongly demanded, more particularly for use with newborn and infant cases.

Living-body side conditions during extracorporeal blood circulation are not constant and blood outflow conditions are likely to change momentarily; however, tubings used for circuit forming purposes, unlike blood vessels, have no content-regulating capability. In apparatuses of the type, therefore, a system is generally employed such that a blood take-off circuit in which a blood feed pump is disposed through a blood reservoir which serves as a buffer against any volumetric change between the blood take-off circuit and the pump is connected to the in-flow side of an artificial lung, with a blood feed circuit connected to the out-flow side of the artificial lung, so that extracorporeal blood circulation is carried out by means of the pump.

Where such apparatus is employed, however, collection of blood into the blood reservoir whose function is to reserve any surplus of the blood in extracorporeal circulation which increases in volume with the progress of blood take-off is made through blood taking as effected with a head provided between the patient and the blood reservoir, and since the head is usually of more than 1 m. It is necessary that the patient must be placed at an elevated position for blood take-off purposes. Naturally, it follows that a longer circuit is required for blood collection; and it is inevitable that a larger priming volume is involved. Further, roller-type or finger type pumps which are usually employed as blood feed pumps have a drawback that squeezing or crushing of the tube by the rollers or fingers has considerable effects upon hematic breakdown and more particularly upon thrombocytopenia and hemolyzation. To replace such roller- or finger-pump, therefore, various types of pumps have been developed which are of such system that a flexible bag, housed in a rigid housing, is expanded and contracted by air pressure. However, all of these are merely of a pulsation type, instead of the conventional roller-or finger-type, and are not significantly contributive toward priming volume reduction.

Another difficulty with the conventional apparatus is that the circuit therein is so complicated that many connectors are used. During any prolonged extracorporeal blood circulation, however, blood is liable to coagulation; therefore, the number of connectors used must be as small as practicable.

SUMMARY OF THE INVENTION

Therefore, it is an object of the invention to provide an apparatus for extracorporeal lung assist such that blood delivery is effected by a reservoir essential for extracorporeal lung assist and without using a pump so that no damage is caused to the blood, and in which the circuit involved is reasonably short, with less priming volume involved.

It is another object of the invention to provide an apparatus for extracorporeal lung assist which requires no blood removable through a head provided between the blood reservoir and a patient.

It is a further object of the invention to provide an apparatus for extracorporeal lung assist which requires no elevated bed and which is convenient in monitoring the patient.

It is a still further object of the invention to provide an apparatus for extracorporeal lung assist which has a simplified extracorporeal circulation circuit with less number of connectors involved and which is quite safe with no possibility of blood coagulation or otherwise.

Accordingly, the invention provides an apparatus for extracorporeal lung assist including pump means having a flexible reservoir housed in a rigid housing, said pump means being adapted to expand and contract said blood reservoir by pumping liquid into and from the housing, thereby repeating cycles of blood feed and blood take-off, a blood take-off circuit connected to the in-flow side of a membrane artificial lung and in which the pump means are disposed, and a blood feed circuit connected to the out-flow side of said artificial lung, said apparatus comprising a liquid circulation circuit connected to said housing of the pump means and in which a flexible liquid reservoir is disposed with a head provided relative to said pump means, and sensor means for detecting the expansion and contraction of said blood reservoir, whereby blood in-flow and out-flow paths may be controlled so that when the blood reservoir is contracted, blood is drawn into the blood reservoir under subpressure in the housing, whereas when the blood reservoir is expanded, blood is discharged from the blood reservoir under pressure developed in the housing.

DETAILED DESCRIPTION OF THE INVENTION

Figure 1:
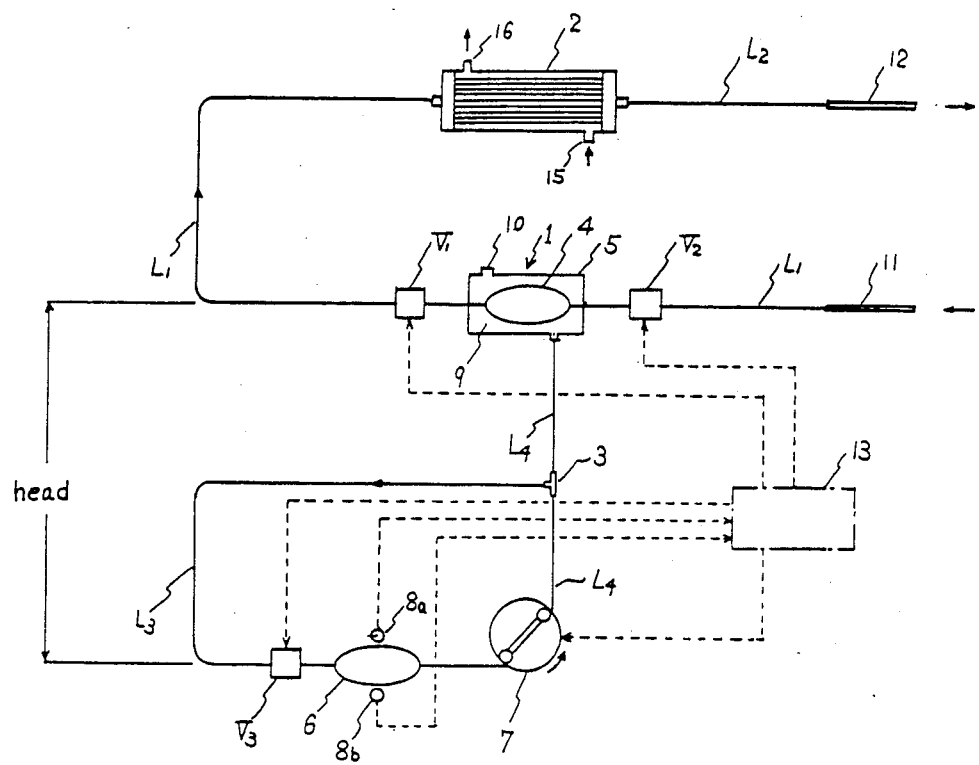
FIG. 1 is a schematic diagram showing a two-catheter system apparatus for extracorporeal lung assist in which blood take-off and blood feed cycles are carried out through two catheters.

FIG. 1 is a schematic view showing a two-catheter system apparatus in which the catheters are employed for blood take-off and blood feed operations respectively. The blood is supplied from a catheter 11 inserted into a vein or artery of a patient (not shown) to a membrane artificial lung 2 through a pump means 1 provided in a blood take-off circuit $L_1$ and comprising a blood reservoir 4 which expands and contracts alternately to perform blood take-off and blood feed. Purified blood as gas-exchanged in the membrane artificial lung is allowed to run along a blood feed circuit $L_2$ for return to the patient through a catheter 12 inserted into his vein or artery. Instead of aforesaid two catheters, a double-tube type catheter may be used so that blood is taken off through one end of the catheter, while blood feed is effected through the other end of the catheter. In order to provide sufficient blood outflow, it is desirable that the front end of the catheter should be inserted adjacent a central vein having a wider interior space, wherever possible. For that purpose, a thin-walled catheter should preferably be used.

The pump means 1 consist of a rigid housing 5 and aforesaid blood reservoir 4 housed therein, which is formed of a flexible material, both expansible and contractable, and which constitutes a portion of the blood take-off circuit $L_1$, with an enclosed space as defined between the blood reservoir 4 and the housing 5. The enclosed space is pressurized or vacuumized by supplying liquid thereinto or discharging same therefrom so that the blood reservoir may be expanded and contracted for blood feed and take-off operation. The blood reservoir 4, made of a well flexible material, such as silicone rubber, polyurethane, flexible vinyl chloride, polyether, or natural or synthetic rubber, has a bag-like or tubular configuration. More especially, a flat bag-like form is preferably used. The volume of the blood reservoir, when expanded, may be suitably determined according to the treatment objective or the patient's condition. Usually, a blood reservoir having a volume equivalent to one-time cardiac output, e.g., 10~16 ml for infant service, or 50~80 ml for adult service, is advantageously used. For the rigid housing in which the blood reservoir is housed is preferred a less stretchable material which is less subject to change in volume under pressure. Examples of such material are plastics, such as polypropylene, polyethylene, rigid vinyl chloride, polycarbonate, acrylics, and polystyrene, and various kinds of metals. In order to observe the operating condition of the blood reservoir housed in the housing, transparent plastics are preferably used. The housing may be of a two-half split construction which permits the blood reservoir to be housed therein, liquid tight, when in use. Or, it may be integral with the blood reservoir. On the top of the housing there is provided an air vent 10.

The membrane artificial lung 2 may be of coil type, plate type, or of hollow fiber type. More specifically, the hollow fiber type is preferably used, since it is easy to fabricate and can be miniaturized. A separation membrane housed in such artificial lung may be a homogeneous membrane formed of a silicone polymer, or a porous membrane formed of such material as polypropylene, polyethylene, polytetrafluoroethylene, or polysulfone. Above all, a recently developed membrane which comprises a porous membrane formed of polysulfone or the like with its pores filled with silicone oil, or with one surface thereof covered with a thin silicone film, is most preferred for use in an artificial lung, because it is not liable to plasma component leakage. Shown by 15 is a feed port for oxygen and shown by 16 is a discharge port therefor.

For artificial lung replacement in the course of extracorporeal blood circulation, it is desirable that a plurality of artificial lungs should be connected in parallel. If, for that purpose, artificial lungs having different membrane areas are so connected, it is possible to use one with a smaller membrane area according to the condition of the patient, thereby effecting such treatment as may be best suited to the patient.

The liquid reservoir 6, as is the case with the blood reservoir 4, is formed of a flexible material, both expansible and contractable, and the available volume of the liquid reservoir, when expanded, may be selectively determined. Usually, it is desirable to employ one having same volume as that of the blood reservoir 4. According to the present invention, it is essential that the liquid reservoir should be disposed at a lower level than the pump means 1 so that a head may be provided between the liquid reservoir and the pump means. By virtue of such head it is possible that liquid as loaded into the enclosed space in the housing under pressure is discharged for supply into the liquid reservoir. In that case, the enclosed space is vacuumized so that the blood is sucked into the blood reservoir. Usually, such head is within the range of 90~100 cm.

A positive displacement pump, e.g. a roller pump or plunger pump, which is able to maintain pressurizing condition when in the state of operation stop is preferably employed as a pump 7 for supplying the liquid in the liquid reservoir 6 into the enclosed space of the housing. More particularly, a multi-roller type roller pump which is less liable to pulsation at the time of pressurizing is preferred from a practical point of view. For the liquid to be encapsulated into the liquid circulation circuit, it is desirable to use such sort of liquid as may involve no hazard if leaked on the blood side, for example, deaerated sterilized water, physiologic salt solution, or grape sugar solution. The liquid is introduced into the liquid circulation circuit through an inlet port (not shown) provided in the circuit.

The expansion and contraction of the blood reservoir 4 is effected in the following manner. The blood circulation circuit consists of the housing 5 in which the blood reservoir is housed, a liquid circuit $L_4$ connected to the flexible liquid reservoir 6 and in which the liquid feed pump 7 is disposed, a branch pipe 3 connected to the liquid circuit, and a liquid circuit $L_3$ connected to the liquid reservoir. The liquid encapsulated into the liquid circulation circuit is supplied to or discharged from the enclosed space 9, whereby the blood reservoir is expanded or contracted under the pressure of the liquid. For this purpose, on the inlet side at least of the pump means in the blood take-off circuit $L_1$ and on the inlet side of the liquid reservoir in the liquid circuit $L_3$ there are respectively provided valves $V_2$ and $V_3$ for ON and OFF control of the respective circuits.

In order to prevent back flow of the blood from the artificial lung 2 to the blood reservoir 4 during a blood take-off cycle, it is desirable to provide valve $V_1$ on the outlet side of the pump means. FIG. 1 shows an embodiment in which valve $V_2$ is provided in the blood take-off circuit. Where a hollow fiber type or plate type artificial lung is used, changes in volume, if any, due to the blood-side pressure are insignificant, and therefore, there may be no possibility of back flow of blood to the blood reservoir, if any negative pressure is applied to the artificial lung in the course of blood takeoff operation, or such back flow, if any, may be insignificant. Where a hollow fiber type or plate type artificial lung is employed, therefore, valve $V_1$ for preventing back flow may be in the blood feed circuit. In the case of a coil type artificial lung, the blood-side volume is liable to considerable change due to pressure; therefore, it is necessary that valve $V_1$ for preventing back flow to the blood reservoir in the course of blood take-off operation should be provided in the blood take-off circuit.

In the FIG. 1 embodiment, the liquid circuit $L_3$ is connected to the branch pipe 3 provided in the circuit $L_4$ which connects between the housing 5 and the liquid reservoir 6, whereby the liquid circulation circuit is formed. Alternatively, the liquid circuit $L_3$ may be connected directly to the housing 5 to form a circuit for circulation between the housing and the liquid reservoir. However, this arrangement, as compared with the FIG. 1 embodiment, is disadvantageous in that the liquid circulation circuit is somewhat longer.

Valves $V_1$, $V_2$, $V_3$ provided in the blood take-off circuit $L_1$ and liquid circuit $L_3$ are usually pinch valves, and these valves are operated by means of air cylinders or hydraulic cylinders. If the valve $V_3$ provided in the liquid circuit $L_3$ is disposed at a higher level than the liquid reservoir, negative pressure may be developed between the liquid reservoir and the valve when the valve is closed, it is possible that air bubbles may develop in the liquid, with the result of some pressure change in the enclosed space of the housing. Therefore, it is desirable that the valve $V_3$ is disposed at a position level with the liquid reservoir.

In order to detect the expansion and contraction of the blood reservoir 4, various methods are available; one method is that detection is made of the expansion and contraction of the liquid reservoir 6 which expands or contracts as the blood reservoir expands or contracts; another method is that changes in pressure within the enclosed space of the housing are detected; another method is that the expansion and contraction of the blood reservoir are detected by means of optical proximity switches; a further method is that gravimeters are used to check the weight of the liquid reservoir or of the pump means; and another method is that either the expansion or the contraction of the blood reservoir is detected by one of the above methods and subsequent cycles of operation are timer-controlled. Above all, the use of capacitance-type or optical proximity switches to detect the expansion and contraction of the liquid reservoir which expands and contracts in synchronism with the blood reservoir is most advantageous because it is very simple and highly reliable. FIG. 1 shows an instance in which two proximity switches 8a, 8b are used to detect the expansion and contraction of the liquid reservoir.

The aforesaid means for detecting the expansion and contraction of the blood reservoir, valves $V_1$, $V_2$, $V_3$, and liquid feed pump 7 are all electrically controllable, so that the entire apparatus can be automatically controlled by control means 13, such as sequencer, microcomputer or the like.

Figure 2:
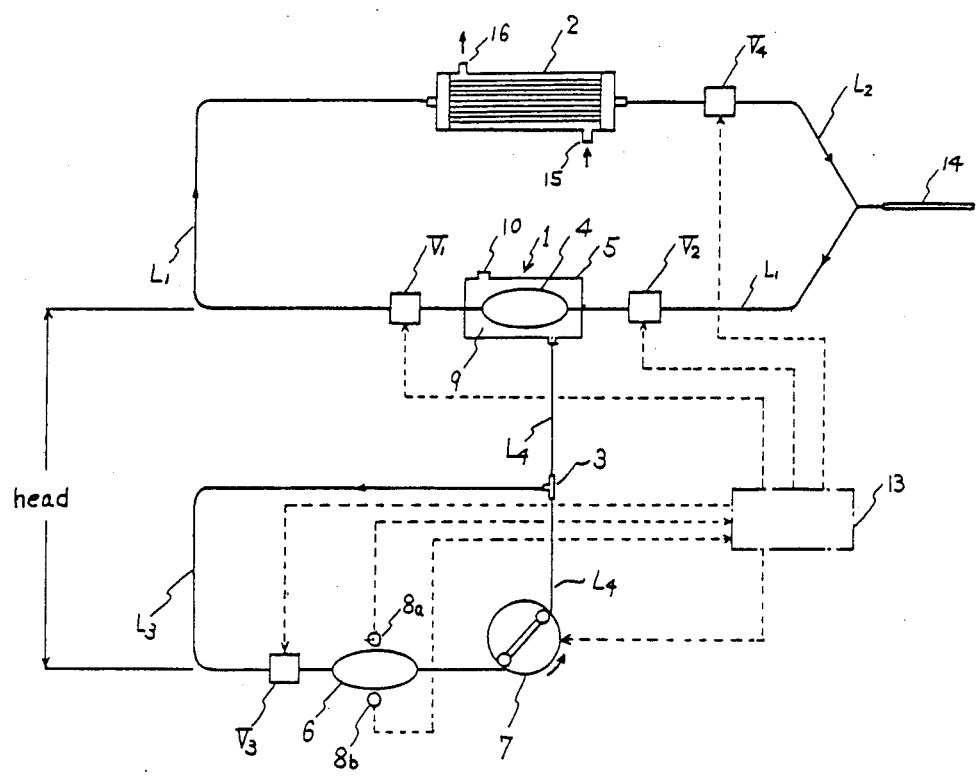
FIG. 2 is a schematic diagram showing a one-catheter system apparatus for extracorporeal lung assist in which blood take-off and blood feed cycles are carried out through one catheter.
Figure 3:
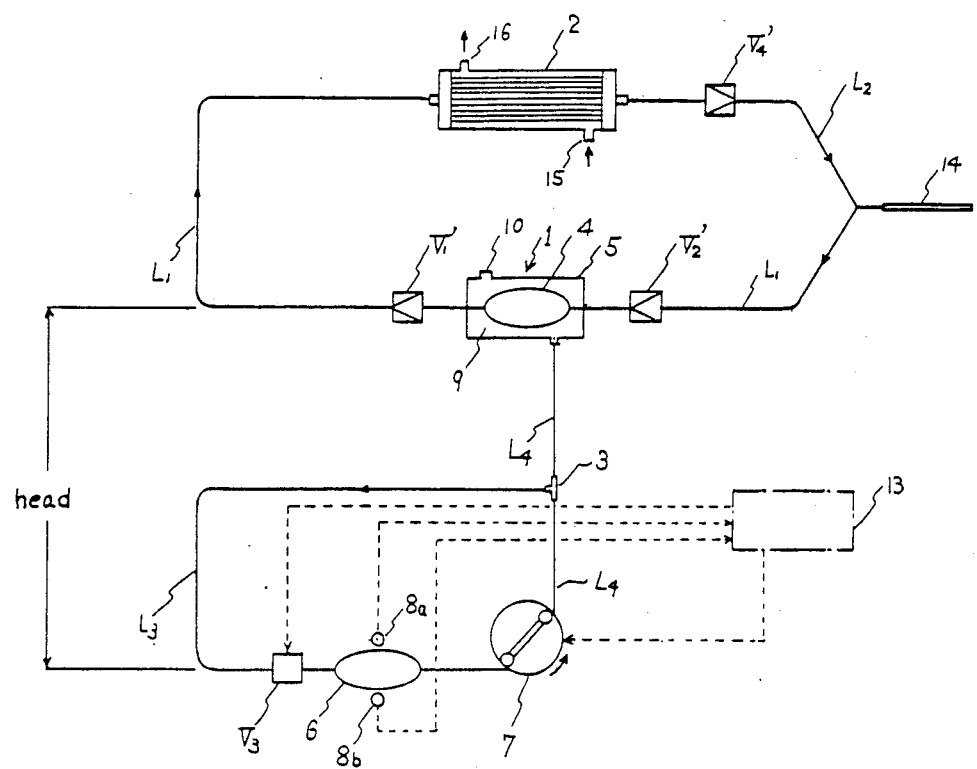
FIG. 3 is a schematic view showing a one-catheter system apparatus for extracorporeal lung assist which incorporates a check valve.
Figure 4:
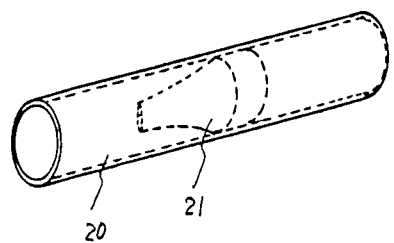
FIG. 4 is a perspective view showing a check valve used in the apparatus according to the invention.

FIG. 2 shows a to-and-fro type arrangement such that blood take-off and blood feed operations are carried out alternately through one catheter 14, the blood take-off circuit $L_1$ and blood feed circuit $L_2$ being connected to the one catheter 14. In this case, with a view to preventing back flow of purified blood into the blood take-off circuit $L_1$ during blood feed operation, and inflow of blood into the blood feed circuit $L_2$ during blood takeoff operation, a valve $V_4$ is provided in the blood feed circuit, said valve $V_4$ being adapted to be turned off during blood feed operation and to be turned on during blood feed operation. The valve $V_4$ is controlled in interlocking relation with the aforesaid means for detecting the expansion and contraction of the blood reservoir. In the case where a hollow fiber type or plate type artificial lung is employed, valve $V_4$ need not be provided, since changes in the blood-side volume, if any, due to pressure may be insignificant. In FIG. 2, parts corresponding to those in FIG. 1 are designated by same reference numerals, and description of such parts is omitted herein. In place of valves $V_1$, $V_2$ provided on the inlet side and outlet side respectively of the pump means 1 in the blood take-off circuit $L_1$, as in the FIG. 1 embodiment, and comparable valves $V_1$, $V_2$ on the inlet side and the outlet side respectively of the pump means 1 in the blood take-off circuit $L_1$, and also valve $V_4$ provided in the blood feed circuit $L_2$, in the FIG. 2 embodiment, check valves set so as to allow the blood to flow from the blood take-off point to the blood feed point may be employed. FIG. 3 is a to-and-fro type embodiment in which check valves are used; $V_1'$, $V_2'$, $V_4'$ are check valves. In FIG. 3, parts corresponding to those in FIG. 2 are designated by same reference numerals, and description of such parts is omitted herein. These check valves should be inexpensive and unlikely to cause blood coagulation during any prolonged extracorporeal blood circulation. FIG. 4 is a perspective view showing a check valve advantageously used in the apparatus of the invention. The check valve shown has a plastic tube 20 having same inner diameter as the tube used for the blood take-off circuit $L_1$, and a thin-wall flat tube 21 having its front end portion sized smaller than the inner diameter of said plastic tube 20 and having the other end thereof enlarged so that its outer diameter is substantially comparable to the inner diameter of said plastic tube, said flat tube 21 being fitted into the interior of said plastic tube. Said other end of the thin-wall flat tube is liquid-tightly fixed with adhesive on the inner periphery of the plastic tube. The thin-wall flat tube 21 must be of a durable material which is well compatible to a living body. Usually, the tube 21 is formed of a polyvinyl chloride or segmented polyurethane material having a thickness of 0.05~0.4 mm. Said thin-wall flat tube is preferably 3~20 mm long.

Figure 5:
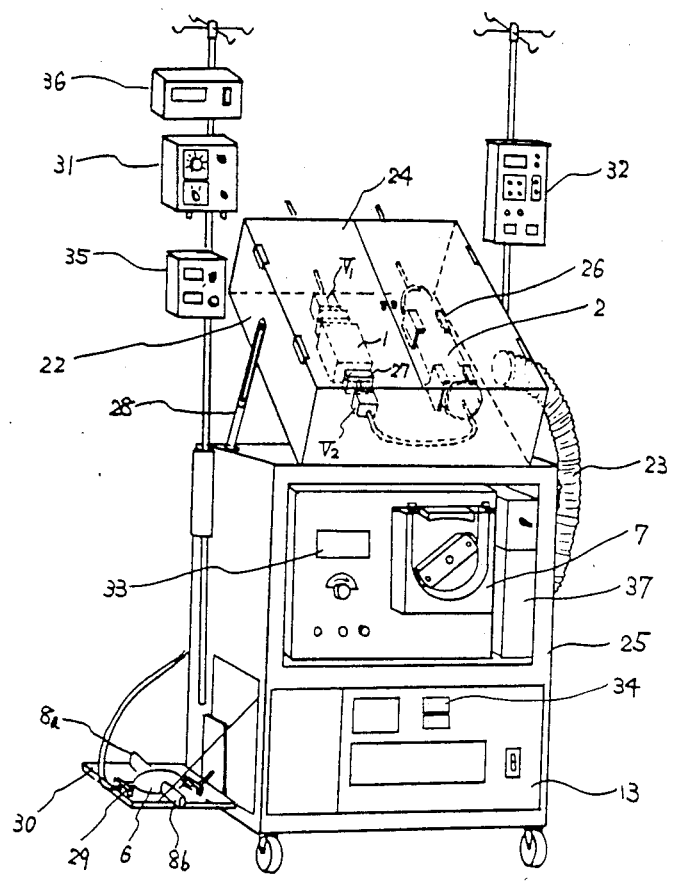
FIG. 5 is a perspective view showing the apparatus of the invention.

FIG. 5 is a perspective view showing the apparatus for extracorporeal lung assist according to the invention, with a closed box 22 mounted on the top of the apparatus body 25. The box is provided with a cover 24 for ready-to-open-close operation. In the box there are provided mounting means 26 for the membrane artificial lung 2 and fittings 27 for fixing the pump means 1 at the front and rear ends thereof, so that the artificial lung and the pump means connected to the circulation circuit can be removably mounted in the box. Air-cylinder type pinch valves $V_1$, $V_2$ are also mounted in the box. The box 22 is connected to a hot-air type heater (not shown) through a duct 23, so that hot air may be supplied into the box so as to keep the interior of the box at temperatures of 39~42° C., for example, in cooperation with preset temperature sensors (not shown). In order to keep the blood take-off and feed position of the patient at same level as the artificial lung so that the circuit involved is made shorter, with less priming volume involved, and concurrently to prevent the development of any abnormal pressure detrimental to the blood and any abnormal flow of blood in the circuit, through a head present between the blood take-off and feed position of the patient and the artificial lung, the apparatus in accordance with the invention has the closed box 22 pivotably mounted on the top of the apparatus body 25. By adjusting the mounting angle of the closed box by means of an expansion member 28 it is possible to coincide the level of the artificial lung with the level of the blood take-off and feed position of the patient. The liquid reservoir 6 disposed with a head provided relative to the pump means 1 is mounted between two mounting elements 29 provided on a mounting base at the lowermost portion of the apparatus body. The liquid reservoir 6 mounted between the two mounting element is adapted to have its expansion and contraction detected by proximity switches 8a, 8b disposed on both sides of the reservoir. On the top of the apparatus body 25 there is mounted a roller pump 7 provided in the liquid circulation circuit (not shown). Shown at 33 is a blood flow meter for per-minute blood flow indication. Adjacent the lower end of the apparatus body there are mounted control means 13. Numeral 34 is thermometer which indicates temperatures in the box. Shown by 31 is an oxygen blender for oxygen-air mixing in a specified ratio for supplying oxygen of a specified concentration to the artificial lung. Shown by 35 is a heater-humidifier for the oxygen from the blender; the oxygen, heated and humidified, is supplied to the artificial lung. Numeral 32 is a control unit for controlling drive switch, etc. for the apparatus. Shown by 36 is a gas monitor for measuring pH, $pCO_2$, $pO_2$, and temperatures. Shown by 37 is a dehumidifier for removing the moisture content of exhaust air.

Figure 6:
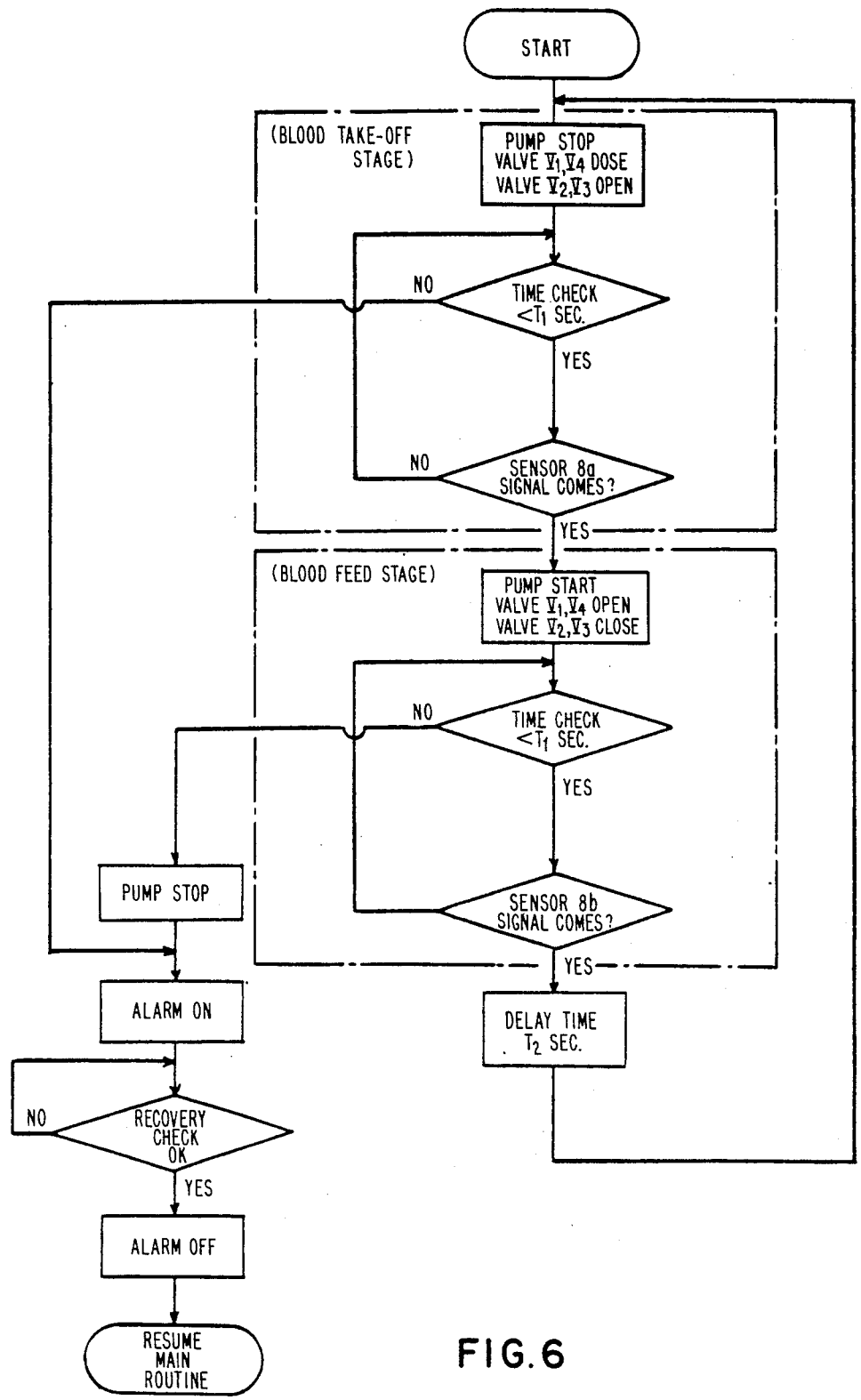
FIG. 6 is a flow chart illustrating the process of sequence control of the apparatus according to the invention.

The manner of operation of the apparatus for extracorporeal lung assist shown in FIG. 2 will now be explained with reference to FIGS. 6 to 8. An electrical control circuit may be of any type inasmuch as it is able to meet the requirements for a sequence control circuit as illustrated in FIG. 6.

Figure 7:
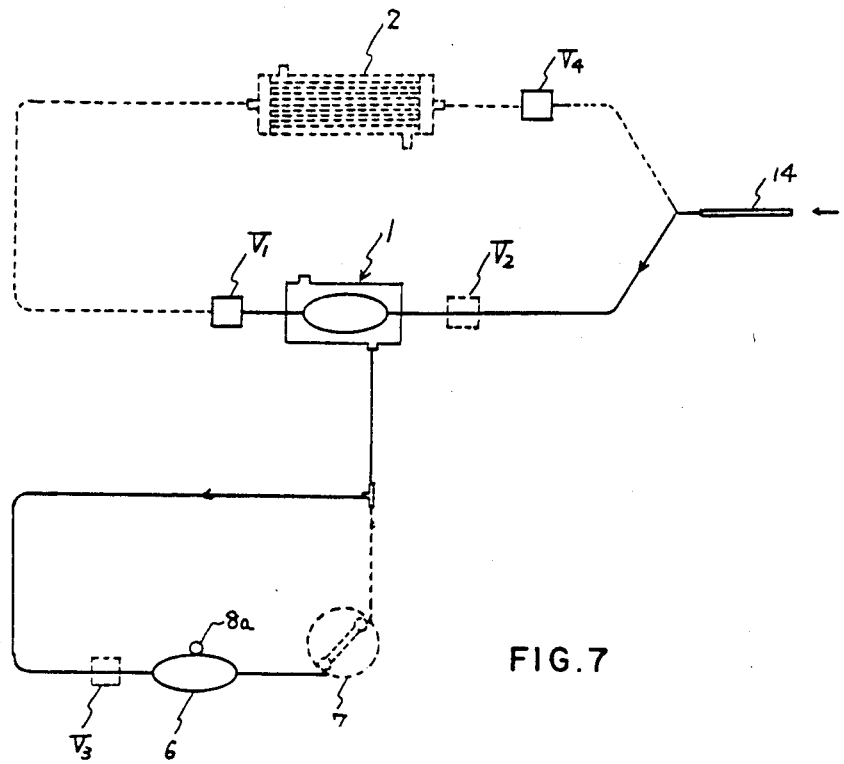
FIGS. 7 and 8 explanatory diagrams showing the process of blood take-off and the process of blood feed respectively.

Blood Take-Off Stage:

When a start switch is turned on, as FIG. 7 shows, valves $V_1$, $V_4$ are closed, and valves $V_2$, $V_3$ are released. At this moment, the roller pump 7 remains stopped.

As the valves are operated, pressurized liquid filled in the enclosed space 9 is caused to drop rapidly into the liquid reservoir 6 disposed at a lower level than the blood reservoir 4. Accordingly, negative pressure develops in the enclosed space and the blood reservoir is expanded so that the blood is sucked into the blood reservoir 4. The blood sucked into the blood reservoir is equivalent in amount to the liquid supplied to the liquid reservoir; therefore, the liquid reservoir expands at same rate as the blood reservoir. A proximity switch 8a for detecting the expansion of the liquid reservoir to a preset position is provided adjacent the liquid reservoir. Upon operation of the proximity switch, the blood take-off operation ends and the valves and the roller pump are controlled for a subsequent blood feed operation.

In blood take-off operation, the liquid reservoir expands at same rate as the blood reservoir because the amount of the liquid supplied to the former is equal to that of the blood sucked into the blood reservoir. If the proximity switch 8a does not turn on in the predetermined time, therefore, there may be some trouble, e.g., blocking or otherwise, in the extracorporeal circuit. In that case, alarm is issued. When the proximity switch turns on, operation proceeds to the blood feed stage.

Figure 8:
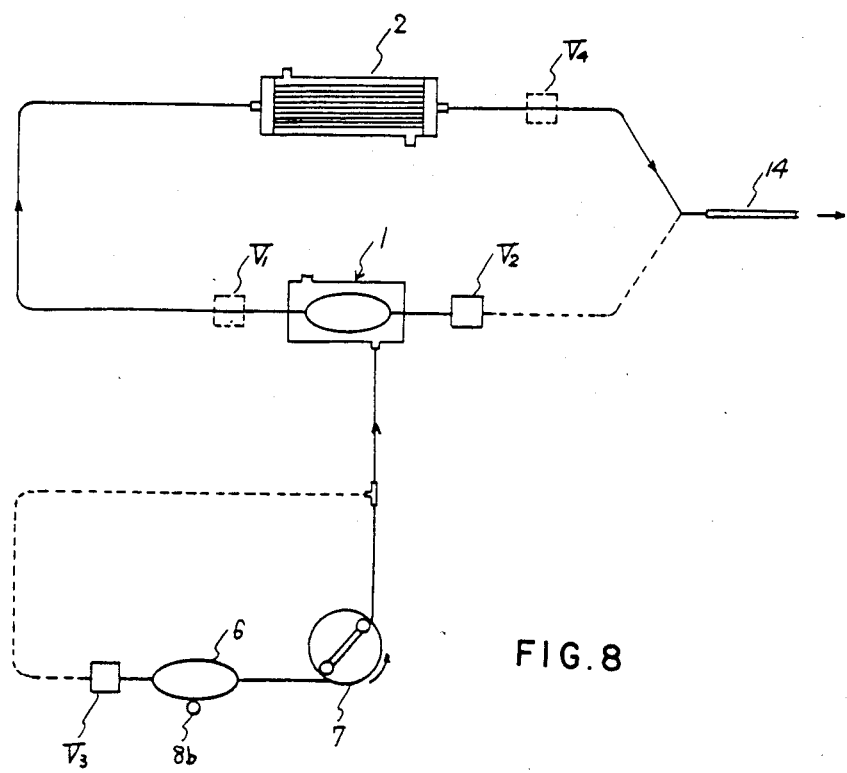

Blood Feed Stage:

In this stage, as FIG. 8 shows, valves $V_1$, $V_4$ are open, and valves $V_2$, $V_3$ are closed. The roller pump 7 operates. The blood reservoir 4, which has been expanded by collecting the blood thereinto, contracts as the liquid from the liquid reservoir 6 is supplied into the enclosed space 9 under pressure through the operation of the roller pump 7. Accordingly, the blood in the blood reservoir is forced out into the artificial lung. As the liquid is supplied into the enclosed space, the blood and liquid reservoirs contract at equal rates, since the blood and the liquid are delivered in equal amounts from the respective reservoirs. Therefore, a proximity switch 8b which detects that the liquid reservoir has contracted to a predetermined position is provided adjacent the liquid reservoir. When the switch 8b turns on, the blood feed operation ends and the valves and the roller pump are controlled for a subsequent blood take-off operation. In this stage of operation, too, if the proximity switch does not turn on in a predetermined time, there may be some trouble in the circuit. In that case, the roller pump 7 is caused to stop running and alarm is issued.

By repeating cycles of above described blood take-off and blood feed operation it is possible to carry out extracorporeal blood circulation automatically and continuously.

In the above described electrically controlled system of extracorporeal circulation, automatic control is a most common practice. However, in case that manual control is preferred during priming or surgical operation, means for changeover from automatic to manual or vice versa may be provided to permit changeover to manual control.

The apparatus of the invention has no roller or finger-pump of conventional type employed in its extracorporeal circulation circuit and is of such novel arrangement that pumping action is performed by a blood reservoir that is essential for an artificial lung. Accordingly, the apparatus has good advantages as follows:

(a) The absence of a roller-type or finger-type pump in the extracorporeal circuit makes it possible to avoid damages to the blood by pump action; therefore, a prolonged use of the apparatus can be assured.

(b) Collection of blood into the blood reservoir need not depend on such gravity blood discharge through the provision of a head as has hitherto been resorted to; therefore, the blood reservoir may be at a higher position than the patient and no such elevated bed as conventionally used to provide a head is required.

(c) Since gravity blood discharge through the provision of a head is not required, a shorter blood circuit can be used, with the result of considerable decrease in priming volume. This permits application of the apparatus for treatment of a patient having a smaller total volume of blood, e.g., newborn or infant.

(d) Blood stream into the artificial lung can be accurately known from the number of cycles operated of the liquid reservoir.

(e) Simplified blood circuit makes it possible to prevent circuit blocking or other similar accidents during any prolonged extracorporeal blood circulation.

(f) The apparatus may be used as a continuous two-catheter system apparatus for extracorporeal lung assist if the circuit on the outlet side of the pump means in the blood take-off circuit is connected to a roller pump for liquid circulation, with all valves left open. Depending upon the condition of the patient, therefore, selection may be suitably made between such continuous system and a system for intermittent blood take-off and blood feed operations.

EXAMPLE

A hollow-fiber type artificial lung having a membrane area of 0.8 m² was prepared by housing into a cylindrical housing, which has a diameter of 36 mm and an effective length of 22 mm, 3800 hollow filaments each of a porous polysulfone hollow fiber having an inner diameter of 320μ and an outer diameter of 480μ, with a 0.5μ thick and substantially poreless silicone rubber layer having no silica content as provided on the inner surface of the hollow fiber. A pump means was also prepared which consisted of a housing formed of a 5 mm thick transparent acrylic plate material and having an internal volume of 125 cc, and a silicone-made flat blood-reservoir having a fill of 15 cc for 100 cc water column and housed in the housing.

The artificial lung and pump means were connected to a silicone tube having an inner diameter of 5 mm and an outer diameter of 7 mm. Said tube was connected at its both ends to a Y-shaped connector to which was coupled a thin-wall 12 F catheter formed of a metal spiral covered with segmented polyethylene. Thus, a to-and-fro system apparatus for extracorporeal lung assist was made which was of such configuration as illustrated in FIG. 2. The appartatus had an extracorporeal circulation circuit of about 2 m and a priming volume of 160 cc including that of the artificial lung.

A vinyl chloride tube having an inner diameter of 10 mm and an outer diameter of 14 mm was used for a liquid circulation circuit. A reservoir identical with aforesaid blood reservoir was employed as a liquid reservoir, which was placed in position with a head of 100 cm relative to the pump means. Capacitance type proximity switches were provided for detecting the expansion and contraction of the liquid reservoir, signals from the proximity switches being utilized to control the operation of a roller pump for liquid circulation and also the open-close operation of air-cylinder type pinch valves arranged so that blood and liquid could flow along the circulation circuit in one direction.

Deaerated Ringer's solution of lactate was filled into the extracorporeal circulation circuit and the artificial lung. Then, the solution was substituted by the blood of a shoat of same litter as the one to be used for experiments.

A 10-days old female shoat having a weight of 3.5 kg was used for the experiments. The catheter was inserted through a left external jugular vein of the shoat and fixed so that the front end of the catheter was positioned adjacent the inlet of the right atrium of heart, and the catether was connected to the extracorporeal circulation circuit. Blood take-off and feed operations were carried out by causing the blood reservoir to expand and contract at a rate of about 31 times/min while time for active coagulation of the blood was kept at 200 sec. Mean blood stream value was 260 cc/min. Into the artificial lung was supplied oxygen of 60% concentration at a flow rate of 1 l/min. Extracorporeal lung assist was carried out under aforesaid conditions for 7 days.

During the extracorporeal blood circulation the gas exchange function of the artificial lung was found stable and maintained at a practically sufficient level. Thrombophilia could hardly be found with the artificial lung, the blood circuit, or the catheter; little hemolyzation was observed. Some transient decrease was found in the number of blood plates, but good recovery was observed later; the number was of the order of 100 thousand/mm³ when at the lowest level and the blood plates were found as having sufficient coagulation capability.

The shoat as relieved of the extracorporeal blood circulation was in full vigor, and nothing was found wrong with the shoat when anatomized one week thereafter.

What is claimed is:

1. An apparatus for extracorporeal lung assist, comprising:
    catheter means for selectively drawing blood from a patient positioned at a pressure head;
    first valve means coupled to said catheter means for regulating the flow of blood received from said catheter means;
    blood pump means at said patient pressure head coupled to said first valve means for pumping blood received from said first valve means, said blood pump means including flexible blood reservoir means, positioned within an interior cavity thereof, said flexible blood reservoir means having a maximum expanded volume, said interior cavity further having a liquid for alternatively contracting and expanding said blood reservoir means in dependence on the volume of fluid provided to said blood pump means;
    second valve means coupled to said blood pump means for regulating the flow of blood received from said blood pump means;
    membrane artificial lung means coupled to receive blood from said second valve means for purifying said blood and selectively providing purified blood to said catheter means;
    third valve means responsive to external signals for regulating said fluid flow;
    flexible flow reservoir means coupled to receive fluid from said third valve means disposed at a pressure head less than said blood pump means, further having a maximum expanded volume approximately equal to said blood reservoir means maximum expanded volume for alternatively expanding and contracting in volume;
    sensor means responsive to said fluid reservoir volume for providing signals indicative of said fluid reservoir volume expansion and contraction;
    fluid pump means responsive to external signals for pumping fluid to said blood pump means;
    control means receiving said sensor signals for providing signals to said third valve means and said fluid pump means so as to control the flow of fluid such that when said fluid reservoir means is expanded, said blood is drawn into said blood reservoir means, and when said fluid is pumped to said blood pump means, said blood is discharged from said blood reservoir means without backflow.

2. The apparatus of claim 1 wherein said catheter means comprises a first catheter for receiving blood from said patient and a second catheter for returning said purified blood thereto.

3. The apparatus of claim 1 further comprising fourth valve means receiving said purified blood from said membrane artificial lung means for selectively providing said purified blood to said catheter means.

4. The apparatus of claim 1 wherein said first, second and third valves are responsive to signals from said control means.

5. The apparatus of claim 1 wherein said first and second valve means comprise flow check valves.

6. The apparatus of claim 1 wherein said membrane artificial lung means comprises a coil type artificial lung.

7. The apparatus of claim 1 wherein said membrane artificial lung means comprises a hollow fiber type artificial lung.

8. The apparatus of claim 1 wherein said sensor means comprises two proximity switches.

9. The apparatus of claim 3 wherein said fourth valve means comprises a check valve.

10. The apparatus of claim 3 wherein said fourth valve means is responsive to external signals from said control means.

* * * * *

UNITED STATES PATENT AND TRADEMARK OFFICE
CERTIFICATE OF CORRECTION

PATENT NO. : 4,650,457

DATED : March 17, 1987

INVENTOR(S) : Tohru Morioka et al

It is certified that error appears in the above-identified patent and that said Letters Patent is hereby corrected as shown below:

On the Title page, item [73],
Please add the following additional Assignees:

-- Tohru Morioka and Hidenori Terasaki, both of Kuramoto-City, Japan;

Signed and Sealed this

Fifteenth Day of June, 1993

Attest:

MICHAEL K. KIRK

Attesting Officer

Acting Commissioner of Patents and Trademarks